(12) United States Patent
Holbrey et al.

(10) Patent No.: US 8,574,368 B2
(45) Date of Patent: Nov. 5, 2013

(54) CONVERSION METHOD

(75) Inventors: John Holbrey, Belfast (GB); Markus Fanselow, Belfast (GB); Kenneth Richard Seddon, Belfast (GB); Lauret Vanoye, Belfast (GB); Anna Zheng, Belfast (GB)

(73) Assignee: Petroliam Nasional Berhard (Petronas), Kuala Lumpur (MY)

( * ) Notice: Subject to any disclaimer, the term of this patent is extended or adjusted under 35 U.S.C. 154(b) by 369 days.

(21) Appl. No.: 12/676,831

(22) PCT Filed: Sep. 3, 2008
(Under 37 CFR 1.47)

(86) PCT No.: PCT/GB2008/050780
§ 371 (c)(1),
(2), (4) Date: Jan. 20, 2011

(87) PCT Pub. No.: WO2009/030950
PCT Pub. Date: Mar. 12, 2009

(65) Prior Publication Data
US 2012/0029247 A1  Feb. 2, 2012

(30) Foreign Application Priority Data
Sep. 6, 2007 (EP) .................... 07253520

(51) Int. Cl.
*C13K 1/02* (2006.01)
(52) U.S. Cl.
USPC .......................................... 127/37
(58) Field of Classification Search
None
See application file for complete search history.

(56) References Cited

U.S. PATENT DOCUMENTS 5,221,357 A  6/1993  Brink
6,824,599 B2  11/2004  Swatloski et al.

FOREIGN PATENT DOCUMENTS

| DE | 10 2004 031 025 | 12/2005 |
| EP | 1 860 201 | 11/2007 |
| JP | 8-299000 | 11/1996 |
| JP | 2006-223152 | 8/2006 |
| WO | WO 2007/057235 | 5/2007 |
| WO | WO 2007/101811 | 9/2007 |

OTHER PUBLICATIONS

Badger. "Ethanol from cellulose: a general review." *Trends*. 2002. pp. 17-21.
Heinze et al. "Ionic Liquids as Reaction Medium in Cellulose Funtionalization." *Macromol. Biosci.* vol. 5. 2005. pp. 520-525.

*Primary Examiner* — Brian J Davis
(74) *Attorney, Agent, or Firm* — Merchant & Gould P.C.

(57) ABSTRACT

A process is described for the preparation of water-soluble cellulose hydrolysis products, which comprises admixing cellulose with an ionic liquid capable of solvating or dissolving at least some of the cellulose, said ionic liquid being a compound comprised solely of cations and anions and which exists in a liquid state at a temperature at or below 150° C., the cations in said ionic liquid having the general formula (I), in which Z represents a nitrogen or phosphorus atom, $R^1$ represents a methyl or ethyl group, each of $R^2$ and $R^3$, which may be the same or different, is selected from $C_{4-3}$alkyl, optionally-substituted benzyl, optionally-substituted phenyl, and $C_{5-7}$ cycloalkyl, and $R^4$ represents $C_{1-8}$ alkyl, optionally-substituted benzyl, optionally-substituted phenyl or $C_{5-7}$cyclohexyl; in which the optional substituents on a benzyl or phenyl ring are one, two or three substituents selected from $C_{1-4}$alkyl or alkoxy groups, halogen atoms and nitro groups; and treating the resulting solvate or solution with an acid in the presence of water, said acid having a pKa in water of less than 2 at 25° C.

19 Claims, No Drawings

CONVERSION METHOD

This application is a National Stage Application of PCT/GB2008/050780, filed 3 Sep. 2008, which claims benefit of Serial No. 07253520.6, filed 6 Sep. 2007 in Europe and which applications are incorporated herein by reference. To the extent appropriate, a claim of priority is made to each of the above disclosed applications.

The present invention relates to a method of hydrolysing cellulose to generate water soluble monosaccharide, disaccharide and oligosaccharide derivatives thereof.

Cellulose is the most abundant biorenewable material on earth. Cellulose consists of polydisperse linear polymeric chains formed by repeated connection of beta-D-glucose building blocks through a 1-4 glycosidic linkage. These linear polymer chains form hydrogen-bonded supramolecular structures that are insoluble in water and most common organic solvents. It is known that hydrolysis of cellulose generates monosaccharide, disaccharide and oligosaccharide products, with glucose usually being the main hydrolysis product. Such products are capable of being fermented to generate alcohols for use as a fuel or a component of a fuel.

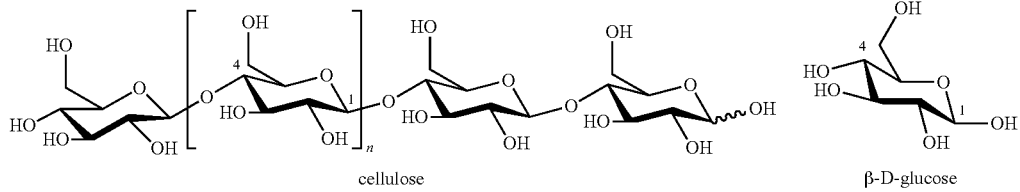

cellulose            β-D-glucose

Glucose in particular is an important intermediate for fermentation to ethanol and other chemicals; therefore, saccharification of cellulose is of interest in the development of biofuels.

Chemical, enzymatic, microbiological and macrobiological catalysts can be used to accelerate the hydrolysis of cellulose under conditions selected to be thermodynamically favourable to product formation. Chemical and enzymatic hydrolysis of cellulose is discussed in "The Encyclopaedia of Polymer Science and Technology", 2nd Ed, J. I. Kroschwitz (Ed in Chief), Wiley (N.Y.), 1985. Thus, cellulose may be hydrolysed using cellulolytic enzymes (cellulase) or harvested filamentous fungi such as *Trichoderma* sp. However, hydrolysing cellulose by chemical methods presents many problems. In general, such methods have involved one of two approaches: dilute acid treatment at high temperatures and pressures (>100° C.) and/or concentrated acid pre-treatment, as described in "Cellulose to Ethanol": A General Review", P. C. Badger, in "Trends in New Crops and New Uses", J. Janick and A. Whipkey (Eds), ASHS Press, Alexandria Va., 2002, 17-21. Dilute acid processes are conducted at high temperature under pressure (for example, using 1% sulphuric acid at 237° C.). Concentrated acid processing typically starts with an initial acid concentration of 10% which is raised to 70% through dewatering at 100° C. and ambient pressure.

Because of the low yields and/or extreme conditions associated with these known processes, there remains the need for an improved method of hydrolysing cellulose by chemical means. Specifically, there is a need for a relatively rapid reaction which may be carried out under relatively mild conditions to give an adequately high conversion to sugars.

It is known that cellulose can be dissolved in certain ionic liquids. For example, U.S. Pat. No. 6,824,599 discloses that cellulose can be dissolved in a hydrophilic ionic liquid in the substantial absence of water or a nitrogen-containing base to forth an admixture, which is then agitated until dissolution is complete, while WO 2005/017001 discloses that wood, straw and other natural lignocellulosic materials can be dissolved in certain ionic liquids under microwave irradiation and/or under pressure. The present inventors have now found that certain ionic liquids containing a certain specific cation can be used in a process for the hydrolysis of cellulose.

Accordingly, the present invention provides a process for the preparation of water-soluble cellulose hydrolysis products, which comprises admixing cellulose with an ionic liquid capable of solvating or dissolving at least some of the cellulose, said ionic liquid being a compound comprised solely of cations and anions and which exists in a liquid state at a temperature at or below 150° C., the cations in said ionic liquid having the general formula:

(I)

in which Z represents a nitrogen or phosphorus atom, $R^1$ represents a methyl or ethyl group, each of $R^2$ and $R^3$, which may be the same or different, is selected from $C_{4-8}$alkyl, optionally-substituted benzyl, optionally-substituted phenyl, and $C_{5-7}$cycloalkyl, and $R^4$ represents $C_{1-8}$ alkyl, optionally-substituted benzyl, optionally-substituted phenyl or $C_{5-7}$cyclohexyl; in which the optional substituents on a benzyl or phenyl ring are one, two or three substituents selected from $C_{1-4}$alkyl or alkoxy groups, halogen atoms and nitro groups; and treating the resulting solvate or solution with an acid in the presence of water, said acid having a pKa in water of less than 2 at 25° C.

Preferably Z represents a nitrogen atom

It is a characteristic of the ionic liquids used in the process of the present invention that the cation of formula I is asymmetric. Thus, $R^1$, and optionally $R^4$, represents a methyl or ethyl group, while each of $R^2$ and $R^3$, and optionally $R^4$, represents a larger group selected from $C_{4-8}$alkyl, optionally-substituted benzyl, optionally-substituted phenyl, and cyclohexyl. A benzyl or phenyl ring may be optionally substituted by one, two or three, for example 1 or 2, of the same or different substituents selected from $C_{1-4}$alkyl or alkoxy, for example methyl or methoxy, groups, halogen atoms, for example chlorine atoms, and nitro groups, but is preferably unsubstituted. Preferably $R^1$ represents a methyl group. Preferably each of $R^2$ and $R^3$ independently represent a $C_{4-8}$, especially a $C_{4-6}$, alkyl group. Preferably each of $R^2$ and $R^3$ represents the same group. In one embodiment, $R^4$ represents a methyl or ethyl group, especially methyl, group. In another embodiment, $R^4$ represents a $C_{3-8}$alkyl, preferably $C_{4-8}$, especially $C_{4-6}$, alkyl group. In one preferred embodiment, each of $R^2$, $R^3$ and $R^4$ represents the same group, especially a $C_{4-8}$, preferably $C_{4-6}$, alkyl group.

Throughout this specification and claims, except where the context requires otherwise, the term "cellulose" should be understood to include both cellulose itself and cellulose-containing material, either in raw or purified form. The cellulose that is to be hydrolysed may be either cellulose which has been refined to any desired degree, or it may be raw or partially-treated cellulosic material, such as cellulosic biomass or municipal waste. It may be used in any form that is amenable to being wetted by a liquid. For example, the cellulose may be present in, or derived from, wood (particularly, wood chips and wood pulp), cotton, rayon, cellulose acetate, paper, linters, grasses such as corn stover or switch grass, or bagasse (sugar cane residue).

The acid used in the process of the invention is a strong acid, having a pKa in water of less than 2, preferably less than 1, preferably 0 or less, at 25° C. An acid with a pKa of 0 is fully dissociated in water, and such acids are preferred for use in the present invention. The acids used in the invention are of the Brönsted (or protonic) type. Suitable acids include for example hydrogen halides, sulfuric acid, nitric acid, strong halocarboxylic acids, halosulfonic acids, tetrafluoroboric acid, heteropolyacids, aryl- and alkyl-sulfonic acids, and halogenated alkyl- and arylsulfonic acids. Examples of suitable acids include, for example, trifluoroacetic acid, p-toluenesulfonic acid, trifluoromethanesulfonic acid (triflic acid), trichloromethanesulfonic acid, hydrochloric acid, hydrobromic acid, hydriodic acid, tetrafluoroboric acid, and sulfuric acid. Preferred acids are trifluoroacetic acid, sulfuric acid, nitric acid, methanesulfonic acid, trifluoromethansulfonic acid, and hydrochloric acid.

The acid may be added in aqueous form, for example dilute aqueous form, or if desired may be anhydrous. Some water is needed in order for the hydrolysis reaction to occur as explained below, and this may either be present in the reaction mixture and/or added along with the acid. A mixture of acids may be used provided that at least one acid has the required acid strength, or the mixture has the required acid strength. In addition to the protonic acid, a Lewis acid may also be added to the reaction mixture if desired. Suitable Lewis acids include metal salts of strong protic acids (pKa less than about 0), in which the metal is for example lithium, potassium, magnesium, zinc, copper, aluminum, tin, antimony, iron, nickel or lanthanum. Suitable examples of such salts include, for example, metal halides, for example aluminum (III) chloride, gallium (III) chloride, indium (III) chloride and zinc (II) chloride; triflates, for example lithium triflate, sodium triflate, magnesium triflate, zinc triflate, aluminum triflate, tin(II) triflate, and copper(II) triflate; tetrafluoroborates, for example zinc (II) tetrafluoroborate, silver (II) tetrafluoroborate, iron (II) tetrafluoroborate, and nickel(II) tetrafluoroborate; and sulfonates, for example zinc p-toluenesulfonate.

Preferably, a catalytic amount of the acid is used. For example, the concentration of the acid in the reaction mixture may be from 0.1-10 wt %. If the reaction mixture before addition of the acid contains any basic material, some of the acid initially added will be neutralised, and sufficient acid needs to be added taking this into account.

The process of the invention is suitably carried out until a desired proportion of the cellulose is converted into water soluble derivatives. Suitably, the treatment with the acid proceeds for up to 96 hours, preferably less than 24 hours, more preferably less than 5 hours, and most preferably less than 1 hour.

The process of the invention may be carried out at any suitable temperature. Admixture of the cellulose with the ionic liquid must, of course, be carried out at a temperature at which the ionic liquid is in fact liquid. Subsequent reaction with the acid may if desired be accelerated by heating; for example, the reaction may be carried out at a temperature in the range 50 to 200° C., preferably 70 to 150° C., for example 90 to 95° C. Heating can be accomplished by any suitable method, for example using conventional thermal methods, microwave heating or employing other sources such as ultrasound or infrared radiation. Preferably the reaction is carried out under atmospheric pressure.

The ionic liquid used in the process of the invention is a compound that consists of cations and anions and that is in a liquid state at a temperature at or below 150° C., preferably at or below 100° C., for example in the range −100° C. to 150° C., preferably −10 to 100° C. It is necessary that the ionic liquid should be capable of dissolving at least some of the cellulose, or should be capable of solvating at least some of the cellulose. Preferably the ionic liquid selected is one in which the cellulose has at least some solubility. When the cellulose is used in the form of biomass, solvation generally leads to swelling of the biomass, and this may be a preferred mode of operation when treating biomass. Alternatively, an ionic liquid may be selected in which the cellulose is readily soluble. On admixture of the cellulose with the ionic liquid, conditions may be chosen such that the cellulose becomes solvated by the ionic liquid; substantially all of the cellulose dissolves to form a homogeneous solution; or some cellulose dissolves while some remains undissolved. Particularly in the latter case, residual solid material may if desired be removed from the solution of cellulose in the ionic liquid by any suitable method. Alternatively, the mixture may be used without further treatment. Suitably, an ionic liquid is selected in which simple solvation or dissolution takes place—i.e. salvation or dissolution without cellulose derivatisation. Naturally, the ionic liquid should be adequately inert in the presence of the strong acid used in the process of the invention; ionic liquids containing basic groups which would neutralise the acid are undesirable.

Any suitable anion may be present in the ionic liquid. Preferably the anion is selected from halide (chloride, bromide, or iodide), cyanate (OCN⁻), sulfate, hydrogen sulfate or nitrate. Preferably the anion is halide, most preferably chloride.

Typically, cellulose is admixed with the ionic liquid in an amount of at least 5% by weight, preferably in an amount of 5 to about 35% weight, for example 5 to 25% percent by weight, especially 10 to about 25% percent by weight.

Stoichiometrically, the hydrolysis reaction requires the presence of one mole equivalent of water for each monomer unit in the cellulose. Cellulose itself contains a certain amount of water, the exact amount depending upon the source and the physical form of the cellulose; usually, prepared cellulose contains at least 10-15% by weight of water. Further water is added to the reaction mixture if aqueous acid is used. However, excessively high amounts of water in the reaction mixture may result in either reduced solubility of the cellulose in the ionic liquid, and/or reduced conversion of cellulose to water-soluble hydrolysis products. Preferably the total water content of the reaction system is such that the weight ratio of water to cellulose is from 1:1 to 1:20, preferably from 1:5 to 1:15, especially about 1:10.

If desired, an additional co-solvent which is compatible with the ionic liquid may be present in the reaction mixture along with the cellulose and the ionic liquid, for example to modify the viscosity of the reaction mixture. Suitable solvents include non-basic polar solvents, for example dimethylsulfoxide, dimethylformamide and sulfolane.

As stated above, the cellulose may be either refined or derived directly from cellulosic biomass, municipal waste or other sources. The water-soluble products of the hydrolysis of cellulose include (a) water soluble oligosaccharides having 3 to 10 D-glucose units; (b) cellobiose; (c) monosaccharides such as glucose and fructose; and (d) glucose derivatives such as levoglucosan, levoglucosenone, levulinic acid, formic acid, 2-furfural, 5-hydroxymethyl-2-furfural, 5-methyl-2-furfural, 2,3-butanedione, glycolaldehyde, glyoxal, 2-furylhydroxymethylketone and pyruval. In general, the most desired products obtainable using the process of the invention are glucose and/or its water soluble oligomers.

When the conversion of cellulose to products has proceeded to the required extent, the reaction mixture may be worked up by any suitable method. For example, water or another solvent, for example an alcohol, e.g. ethanol, may be added to the reaction mixture in order to precipitate any residual cellulose or any insoluble hydrolysis products. Where the ionic liquid is hydrophilic and water is added, an aqueous solution of the ionic liquid and the water-soluble hydrolysis products may be produced. Preferably, the ionic liquid used in the process of the invention is at least partially recovered and reused in the process of the invention. If necessary, any solid material, for example comprising undissolved or unconverted cellulose and/or water insoluble cellulose hydrolysis products, may be separated by any suitable method, and if desired, recycled back to the start of the process.

Alternatively, the reaction mixture or any fraction thereof may be used directly in any subsequent step required to process the products of the reaction.

In a preferred embodiment of the process of the invention, subsequent processing of the products formed is carried out to produce lower alcohols, particularly ethanol, suitable for use as a biofuel. Thus, in a further embodiment, the invention provides a process for the preparation of water-soluble cellulose hydrolysis products, which comprises admixing cellulose with an ionic liquid capable of solvating or dissolving at least some of the cellulose, said ionic liquid being a compound comprised solely of cations and anions and which exists in a liquid state at a temperature at or below 150° C., the cations in said ionic liquid having the general formula I as defined above; and treating the resulting solvate or solution with an acid in the presence of water, said acid having a pKa in water of less than 2 at 25° C., and converting at least part of the resulting product into one or more alcohols. The water-soluble cellulose hydrolysis products may for example be converted into alcohols by fermentation.

The following Examples illustrate the invention.

EXAMPLE 1

10 g of tributylmethyl ammonium chloride were placed in a round bottomed flask and heated to 120° C., upon which it melted. 0.1 ml concentrated CF$_3$COOH was added dropwise through a syringe, and 0.1 g Miscanthus (milled to 0.5 mm) was added and stirred, the stirring speed set to maximum in order to effect efficient wetting of the substrate. Samples were taken periodically and analysed by refractive index high performance chromatography. The yield of water-soluble products having glucose end-groups was 8.7% after 150 mins.

EXAMPLES 2 TO 6

The general method of Example 1 was repeated except that the trifluoroacetic acid was replaced by the same volume of other acids. The results are given in the following Table.

TABLE

| Example No. | Acid used | Yield of product (%) |
|---|---|---|
| 2 | conc. HCl | 13.8% after 150 mins. |
| 3 | conc. H$_2$SO$_4$ | 10.8% after 90 mins. |
| 4 | conc. HNO$_3$ | 23.7% after 150 mins. |
| 5 | CH$_3$SO$_3$H | 10.3% after 90 mins. |
| 6 | CF$_3$SO$_3$H | 9.2% after 90 mins. |

The invention claimed is:

1. A process for the preparation of water-soluble cellulose hydrolysis products, which comprises admixing cellulose with an ionic liquid capable of solvating or dissolving at least some of the cellulose, said ionic liquid being a compound comprised solely of cations and anions and which exists in a liquid state at a temperature at or below 150° C., the cations in said ionic liquid having the general formula:

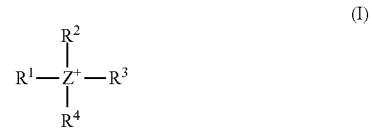

in which Z represents a nitrogen or phosphorus atom, R$^1$ represents a methyl or ethyl group, each of R$^2$ and R$^3$, which may be the same or different, is selected from C$_{4-8}$alkyl, optionally-substituted benzyl, optionally-substituted phenyl, and C$_{5-7}$cycloalkyl; and R$^4$ represents C$_{1-8}$alkyl, optionally-substituted benzyl, optionally-substituted phenyl or C$_{5-7}$cyclohexyl; in which the optional substituents on a benzyl or phenyl ring are one, two or three substituents selected from C$_{1-4}$alkyl or alkoxy groups, halogen atoms and nitro groups; and treating the resulting solvate or solution with an acid in the presence of water, said acid having a pKa in water of less than 2 at 25° C.

2. A process as claimed in claim 1, in which said ionic liquid is one in which the cellulose has at least some solubility.

3. A process as claimed in claim 1, in which the acid has a pKa in water of 0 or less at 25° C.

4. A process as claimed in claim 1, in which the acid is selected from hydrogen halides, sulfuric acid, nitric acid, halocarboxylic acids, halosulfonic acids, tetrafluoroboric acid, heteropolyacids, aryl- and alkyl-sulfonic acids, and halogenated alkyl- and arylsulfonic acids.

5. A process as claimed in claim 4, in which the acid is p-toluenesulfonic acid, trifluoromethanesulfonic acid, trichloromethanesulfonic acid, trifluoroacetic acid, hydrochloric acid, hydrobromic acid, hydriodic acid, tetrafluoroboric acid, or sulfuric acid.

6. A process as claimed in claim 4, in which the acid is trifluoroacetic acid, sulfuric acid, nitric acid, methanesulfonic acid, trifluoromethansulfonic acid, or hydrochloric acid.

7. A process as claimed in claim 1, in which the reaction with the acid is carried out at a temperature in the range of from 50 to 200° C.

8. A process as claimed in claim 1, in which Z represents a nitrogen atom.

9. A process as claimed in claim 1, in which $R^1$ represents a methyl group.

10. A process as claimed in claim 1, in which each of $R^2$ and $R^3$ independently represent a $C_{4-8}$ alkyl group.

11. A process as claimed in claim 1, in which each of $R^2$ and $R^3$ represents the same group.

12. A process as claimed in claim 1, in which $R^4$ represents a $C_{1-8}$ alkyl group.

13. A process as claimed in claim 1, in which each of $R^2$, $R^3$ and $R^4$ represents the same group.

14. A process as claimed in claim 12, in which $R^4$ represents a methyl group.

15. A process as claimed in claim 1, in which the anion of the ionic liquid is halide, cyanate, sulfate, hydrogen sulfate or nitrate.

16. A process as claimed in claim 1, in which the cellulose is admixed with the ionic liquid in an amount of from 5 to 35% weight.

17. A process as claimed in claim 1, in which the water content of the reaction system is such that the weight ratio of water to cellulose is from 1:1 to 1:20.

18. A process as claimed in claim 17, in which the water content of the reaction system is such that the weight ratio of water to cellulose is from 1:5 to 1:15.

19. A process for the preparation of one or more alcohols, which comprises carrying out a process as claimed in claim 1, and converting at least part of the resulting product into one or more alcohols.

* * * * *

UNITED STATES PATENT AND TRADEMARK OFFICE
CERTIFICATE OF CORRECTION

| | | |
|---|---|---|
| PATENT NO. | : 8,574,368 B2 | Page 1 of 1 |
| APPLICATION NO. | : 12/676831 | |
| DATED | : November 5, 2013 | |
| INVENTOR(S) | : John Holbrey et al. | |

It is certified that error appears in the above-identified patent and that said Letters Patent is hereby corrected as shown below:

On the Title Page

Item (73) Assignee: "Petroliam Nasional Berhard (Petronas)" should read – Petroliam Nasional Berhad (Petronas)

Signed and Sealed this
Sixth Day of January, 2015

Michelle K. Lee
*Deputy Director of the United States Patent and Trademark Office*